United States Patent
Miklos et al.

(10) Patent No.: US 6,267,749 B1
(45) Date of Patent: Jul. 31, 2001

(54) SINGLE USE SYRINGE WITH BREAKAWAY PLUNGER

(75) Inventors: Kodobor Miklos, Nemvetor út; Filippo Filippe, Jószerenesét tér, both of (HU)

(73) Assignee: Safeguard Medical Limited, Woburn, MA (US)

( * ) Notice: Subject to any disclaimer, the term of this patent is extended or adjusted under 35 U.S.C. 154(b) by 0 days.

(21) Appl. No.: 09/473,865

(22) Filed: Dec. 28, 1999

Related U.S. Application Data

(60) Provisional application No. 60/114,100, filed on Dec. 29, 1998.

(51) Int. Cl.⁷ ................................................. A61M 5/00
(52) U.S. Cl. ............................................. 604/110; 604/218
(58) Field of Search ........................... 604/110, 218, 604/220, 228, 187

(56) References Cited

U.S. PATENT DOCUMENTS

| | | | |
|---|---|---|---|
| 4,775,364 | 10/1988 | Alles | 604/110 |
| 4,919,652 * | 4/1990 | Alter et al. | 604/110 |
| 4,950,240 | 8/1990 | Greenwood et al. | 604/110 |
| 5,000,735 | 3/1991 | Whelan | 604/110 |
| 5,004,460 | 4/1991 | Gimeno | 604/228 |
| 5,045,063 * | 9/1991 | Spielberg | 604/218 X |
| 5,047,017 | 9/1991 | Koska | 604/110 |
| 5,205,824 | 4/1993 | Mazur | 604/110 |
| 5,242,400 * | 9/1993 | Blake, III et al. | 604/110 |
| 5,259,840 * | 11/1993 | Boris | 604/218 X |
| 5,304,138 | 4/1994 | Mercado | 604/110 |
| 5,308,331 | 5/1994 | Avila et al. | 604/110 |
| 5,318,537 | 6/1994 | Van Der Merwe | 604/110 |
| 5,344,403 | 9/1994 | Lee | 604/110 |
| 5,346,474 | 9/1994 | King | 604/110 |
| 5,380,285 | 1/1995 | Jenson | 604/110 |
| 5,401,249 | 3/1995 | Shields | 601/187 |
| 5,423,756 | 6/1995 | van der Merwe | 605/110 |
| 5,478,314 | 12/1995 | Malenchek | 604/110 |
| 5,531,691 | 7/1996 | Shonfeld et al. | 604/110 |
| 5,709,659 | 1/1998 | Bennwik et al. | 604/110 |
| 5,814,017 * | 9/1998 | Kashmer | 604/110 |

* cited by examiner

*Primary Examiner*—John D. Yasko
(74) *Attorney, Agent, or Firm*—Elizabeth E. Nugent; Choate, Hall & Stewart

(57) ABSTRACT

A syringe is provided that comprises a plunger which is adapted to be locked in place when it is fully compressed. The plunger comprises a frangible section which has a breaking strength less than the holding strength of the locking structure. Thus, if an attempt is made to withdraw the plunger and reuse the syringe after the plunger has been fully compressed, the plunger will break, rather than withdrawing from the syringe barrel.

7 Claims, 3 Drawing Sheets

SINGLE USE SYRINGE WITH BREAKAWAY PLUNGER

This application claims benefit and priority of U.S. Provisional Application 60/114,100, "Single Use Syringe with Breakaway Plunger," filed Dec. 29, 1998. This related application is incorporated herein by reference.

FIELD OF THE INVENTION

This invention relates generally to a single use syringe device and more specifically to a syringe device having a plunger which breaks if an attempt is made to reuse the syringe.

BACKGROUND OF THE INVENTION

The increasing awareness of the importance of sterility in hypodermic devices has led to the development of disposable syringes. The initial sterility of these devices, coupled with their low cost, has led to their widespread use in preference to reusable devices requiring sterilization before reuse. But this widespread use of disposable syringes has created problems. By their economic nature, inexpensive devices, utilized in high numbers, tend to make inventory controls on new and used devices difficult and prone to breakdown. It is not uncommon for syringes, along with the attached needles, to find their way into unauthorized hands. Once control is lost, these devices may be reused without sterilization.

Reuse of hypodermic syringes, intended for a single use only, is an important factor in the transfer of contagious diseases and facilitation of drug abuse. Intravenous drug users who routinely share and reuse syringes are a high risk group with respect to HIV and the hepatitis virus. Easy access to the devices further facilitates illegal drug use. In addition, the effects of repeated uses of syringe products may be responsible for the spread of many other diseases.

One solution to these problems is to develop syringes which functionally self-destruct after a single application. While the availability of non-reusable syringes will not necessarily stop illegal drug use, it can prevent sharing of contaminated hypodermic syringes and thus help reduce the spread of diseases.

Many approaches have been made to prevent and limit reuse. Initially, syringe designs incorporated features facilitating an explicit destructive act. Thus, by the application of force, the syringe became inoperable. Other designs included special structures to lock the device in a position preventing reuse. Some designs utilized locks incorporated in the barrel section of the syringe, requiring full extension to engage the device. Other designs require the syringe to be prefilled, and do not allow filling of the syringe in the conventional manner. Additional designs required multiple parts and careful assembly. Further, many of these designs relate to syringes which can be rendered inoperable after a single use, rather than syringes which are automatically rendered inoperable by the act of using the syringe a first time. Thus, the safety features may be easily defeated by an unscrupulous user who wishes to reuse the syringe.

The ideal syringe design would incorporate a locking mechanism that would allow conventional use of the syringe (e.g., normal filling operations). In addition, the design would be simple to operate, not requiring any special training. The design should be able to utilize standard hypodermic needles. The design should be inexpensive and reliable and should encourage the full and complete elimination of valuable medication. Finally, the design should automatically render the syringe inoperable for a second use after it is used in a conventional manner on its first use.

SUMMARY OF THE INVENTION

In one aspect of the present invention, a syringe is provided that comprises a plunger which is adapted to be locked in place when it is fully compressed. The plunger comprises a frangible section which has a breaking strength less than the holding strength of the locking structure. Thus, if an attempt is made to withdraw the plunger and resuse the syringe after the plunger has been fully compressed, the plunger will break, rather than withdrawing from the syringe barrel. The locking mechanism may comprise a detent at the distal end of the plunger and a locking ring at the distal end of the barrel. The barrel may include a fitting (e.g., a Luer fitting) for attaching a hypodermic needle, and the syringe may be designed to completely expel any fluid upon fully compressing the plunger.

BRIEF DESCRIPTION OF THE DRAWING

The invention is described with reference to the several figures of the drawing, in which.

DETAILED DESCRIPTION

The invention is described hereinbelow with reference to a syringe of the type described in U.S. Pat. No. 5,814,017 to Kashmer, which is incorporated herein by reference. It will be apparent to those skilled in the art, however, that the breakaway plunger of the invention may be used with any structure which firmly holds the distal (patient) end of a syringe plunger once the syringe has been used. Such modifications are considered to fall within the scope of the present invention.

Figure 1:
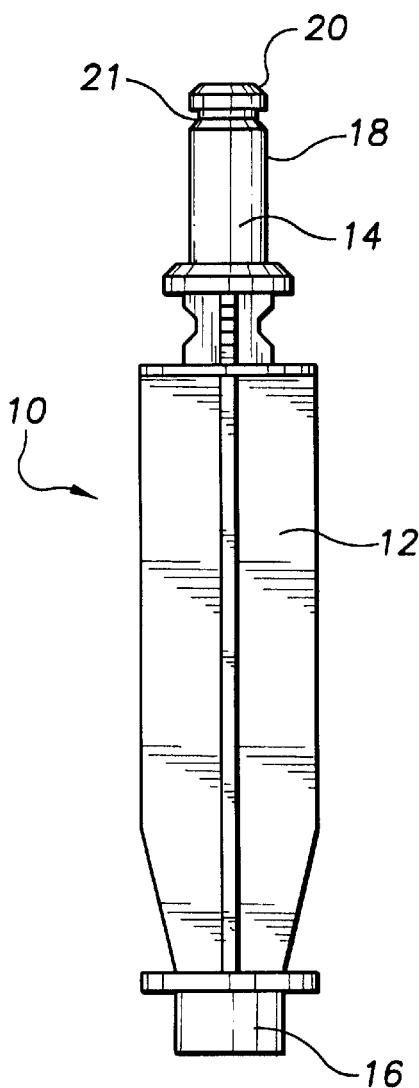
FIG. 1 shows a breakaway plunger for a syringe according to the invention.
Figure 1A:
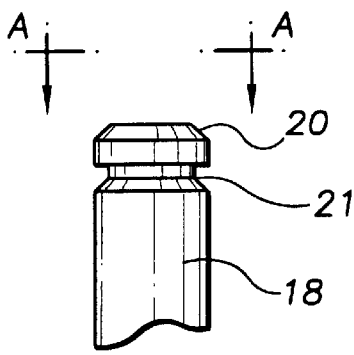
FIGS. 1A–1D show detail views of the plunger of FIG. 1.
Figure 1B:
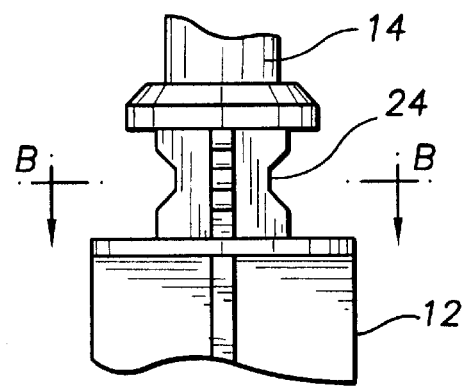
Figure 1C:
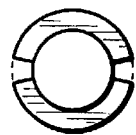
Figure 1D:
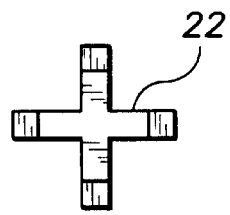

FIG. 1 shows a plunger 10 for a syringe according to the invention. FIGS. 1A and 1B show details of the distal end and the breakaway section of the plunger, and FIGS. 1C and 1D show cross sections as indicated by arrows A—A and B—B, respectively. The plunger assembly 10 includes an elongate plunger rod 12 and a piston member 14, which is preferably but not necessarily elastomeric. The proximal portion of the plunger rod 12 connects to an enlarged head portion 16 designed to be grasped or pushed by the user's thumb. The distal portion of the plunger rod 12 connects to a circular end member 18, which further leads to a tapered plunger tip 20 having a generally circular cross section and including a detent 21 for locking the plunger tip as described in detail in U.S. Pat. No. 5,814,017. As shown in FIG. 1C, the tip may comprise V-cuts or other structures for facilitating compression of the tip. FIG. 1D illustrates how the plunger rod 12 may be formed by a plurality of radially extending rib members 22 that longitudinally extend between head portion 16 and circular end member 18.

Shown in detail in FIG. 1B, the plunger according to the invention comprises a breakaway section 24. This may be a narrowed section as shown, or may be a sharp notch, a section of different material, or any other construction which provides the plunger 10 with a frangible section whose breaking strength may be controlled.

Figure 2:
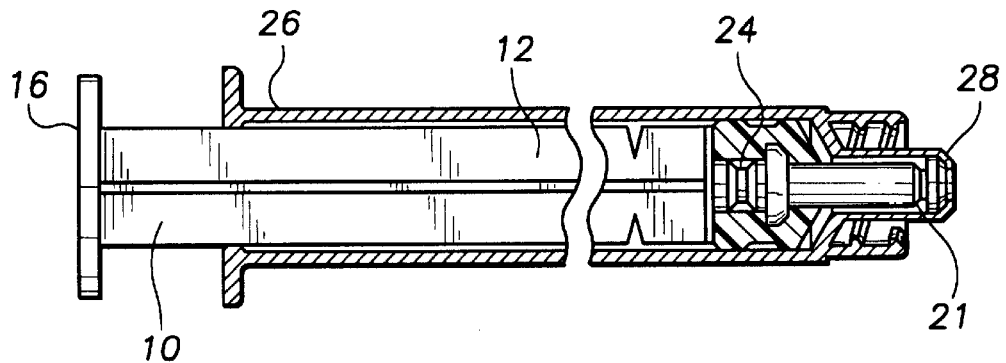
FIG. 2 shows a cutaway view of an assembled syringe according to the invention.

FIG. 2 shows the plunger of FIG. 1 disposed in a syringe barrel 26 to form a syringe according to the invention. The barrel 26 will preferably comprise a Luer fitting or the like for securing a hypodermic needle to the end of the syringe. The barrel 26 comprises a locking ring 28 for engaging the detent 21 to lock the plunger in the distal position.

Figure 3A:
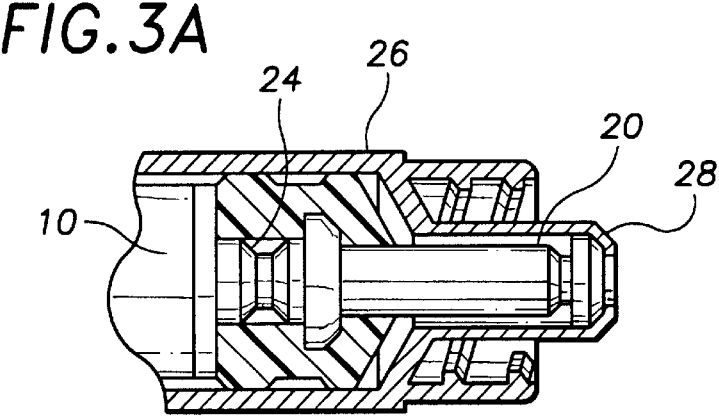
FIGS. 3A–3F show a series of detail views showing the action of the syringe of the invention.
Figure 3B:
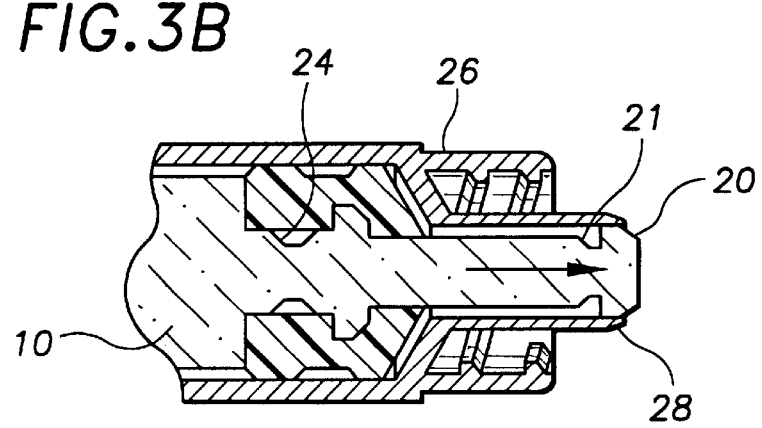
Figure 3C:
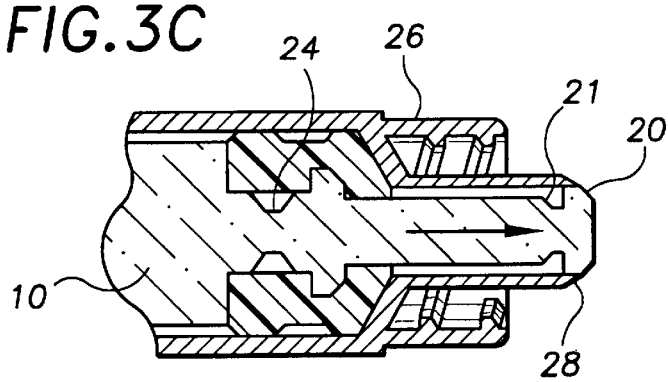
Figure 3D:
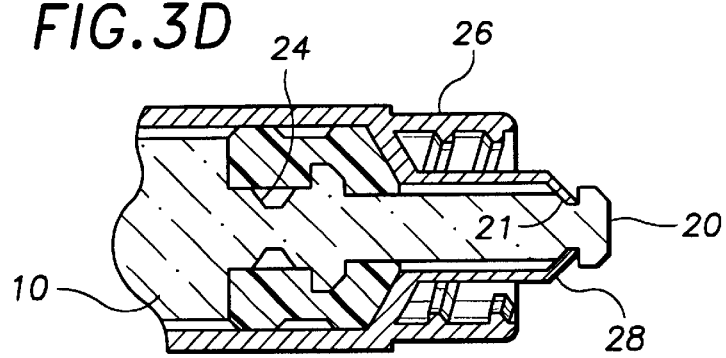
Figure 3E:
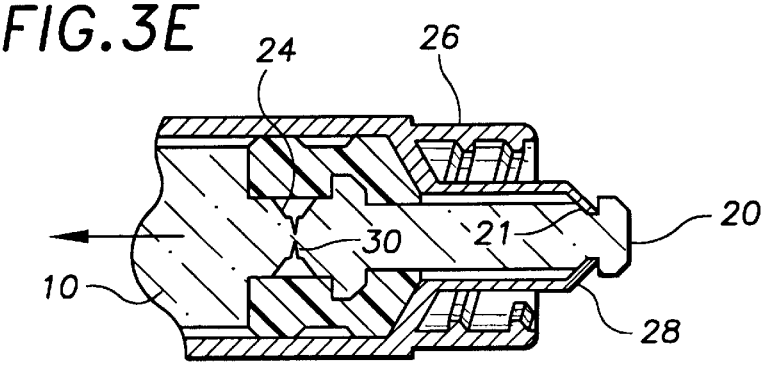
Figure 3F:
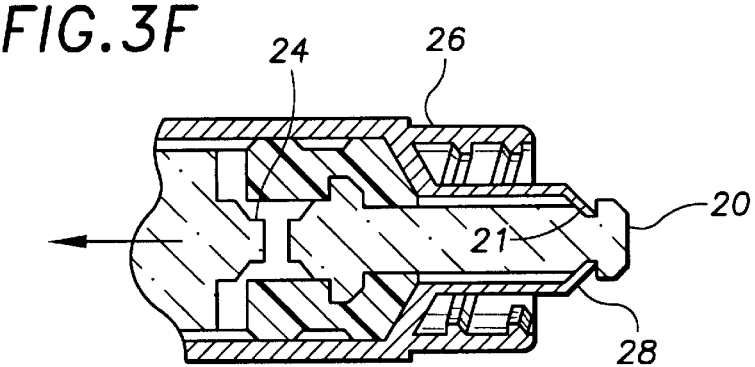

FIGS. 3A–3F illustrate the action of the syringe of the invention. FIG. 3A shows the plunger 10 near the distal end of the syringe barrel 26. The plunger tip 20 is just proximal to the locking ring 28. As the plunger 10 is moved distally within the barrel 26, the locking ring 28 expands, as shown in FIG. 3B. FIG. 3C shows the plunger 10 and barrel 26 just before engagement of the lock. As shown in FIG. 3D, the locking ring 28 snaps inward to engage the detent 21, providing resistance to any proximal motion of the plunger 10. If an attempt is made to force the plunger 10 in the proximal direction (e.g., to reuse the plunger), a crack 30 develops in the frangible section 24, as shown in FIG. 3E, and the plunger 10 breaks into two pieces, as shown in FIG. 3F.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A single-use syringe, comprising:

a barrel having proximal and distal ends, a longitudinal channel therethrough, and a port at its distal end;

a plunger adapted to move along said longitudinal channel, at least a portion of the plunger being adapted to conform to an inner surface of the barrel, the plunger comprising a frangible section adapted to break upon application of a selected longitudinal tension; and an engageable lock for holding a portion of the plunger distal to said frangible section, wherein said lock is capable of holding the portion of the plunger in opposition to a force in excess of said selected longitudinal tension, whereby upon engagement of the lock, a proximal force in excess of said selected longitudinal tension applied to the proximal end of the plunger will cause the frangible section to break.

2. The single-use syringe of claim 1, further comprising means at the barrel port for attaching a hypodermic needle.

3. The single-use syringe of claim 2, wherein said attaching means comprise a Luer fitting.

4. The single-use syringe of claim 1, wherein said lock comprises a locking pin having at least one detent at the distal end of the plunger, and a locking ring at the distal end of the barrel, the locking ring being adapted to engage the locking pin when the plunger is moved in the distal direction within the barrel.

5. The single-use syringe of claim 1, wherein said lock engages when the plunger is moved to the limit of its travel in the distal direction within the barrel channel.

6. The single-use syringe of claim 1, wherein the longitudinal channel in the barrel is adapted to be filled with fluid, which is expelled through the barrel port by distal motion of the plunger.

7. The single-use syringe of claim 6, wherein the fluid is completely expelled and the lock is engaged when the plunger is moved to the limit of its travel in the distal direction within the barrel channel.

* * * * *